United States Patent [19]

Pelosi, Jr.

[11] 4,031,113

[45] June 21, 1977

[54] 5-[5-(4-CHLOROPHENYL)-2-FURANYL]-DIHYDRO-2(3H)-FURANONE

[75] Inventor: Stanford S. Pelosi, Jr., Norwich, N.Y.

[73] Assignee: Morton-Norwich Products, Inc., Norwich, N.Y.

[22] Filed: Mar. 29, 1976

[21] Appl. No.: 671,095

[52] U.S. Cl. .............................. 260/343.6; 424/279
[51] Int. Cl.² ........................................ C07D 407/04
[58] Field of Search ................................. 260/343.6

[56] References Cited

UNITED STATES PATENTS 2,368,366  1/1945  Kyrides et al. .................... 260/344

OTHER PUBLICATIONS

Gaylord, Reduction with Complex Metal Hydrides (Interscience, N. Y., 1956) pp. 373, 507–509.

*Primary Examiner*—Cecilia M. S. Jaisle
*Attorney, Agent, or Firm*—Anthony J. Franze

[57] ABSTRACT

The compound 5-[-(4-Chlorophenyl)-2-Furanyl]Dihydro-2(3H)-Furanone is a useful anti-inflammatory agent.

1 Claim, No Drawings

5-[5-(4-CHLOROPHENYL)-2-FURANYL]DIHYDRO-2(3H)-FURANONE

This invention is concerned with chemical compounds and more particularly with the compound 5-[5-(4-chlorphenyl)-2-furanyl]dihydro-2(3H)-furanone.

The compound of this invention possesses pharmacological properties. It is particularly useful as an anti-inflammatory agent as evidenced by its ability to inhibit adema induced by the administration of carragennin. Thus when it is administered orally at a dose of 300 mg/kg suspended in a vehicle such as aqueous methyl cellulose to rats receiving carrageenin, edema provoked by that substance is inhibited [Winter et al., P.S.E.B.M. 114:544 (1964)].

The compound of this invention can be combined in various pharmaceutical forms such as tablets, capsules, dragees, suspensions and the like using excipients and adjuvants commonplace in the pharmaceutical art and with which there is no incompatibility.

In order that this invention may be readily available to and understood by those skilled in the art, the following method for its preparation is supplied:

A. Methyl 4-[5-(4-Chlorophenyl)-2-furanyl]-4-oxobutanate

To a stirring mixture of 62 g (0.50 mole) of $AlCl_3$ in 375 ml of 1,2-dichlorethane was added portionwise 75 g (0.5 mole) of 3-carbomethoxypropionyl chloride while keeping the temperature below 25° by means of an ice bath. The reaction mixture was cooled to 15° and a solution of 89 g (0.5 mole) of 5-(4-chlorphenyl)furan in 250 ml of 1,2-dichloroethane was added dropwise with large volumes of HCl gas being evolved and the temperature rising to 30°. The reaction mixture was stirred at ambient temperature for one hour and then added to 1000 ml of ice water. The organic layer was separated and the aqueous layer extracted with dichlormethane. The combined organic layers were washed with 1000 ml of 6% sodium carbonate solution, with 1000 ml of water and dried over $MgSO_4$. The solvent was removed on the Calab evaporator yielding a residual oil which was extracted several times with refluxing hexane. The hexane extracts were cooled to yield a solid which was filtered, washed twice with 6% sodium carbonate solution, recrystallized from hexane and air dried to yield 7 g (5%). An analytical sample was prepared by drying a sample in a vacuum pistol at room temperature, m.p. 99°–100°.

Anal. Calcd. for $C_{15}H_{13}ClO_4$: C, 61.55; H, 4.48; Found: C 61.49; H, 4.50.

B. 5-[5-(4-Chlorophenyl)-2-furanyl]dihydro-2(3H)-furanone

A solution of 11 g (0.038 mole) of A. and 150 ml of 95% dioxane/$H_2O$ was treated portionwise with 2.8 g (0.076 mole) of $NaBH_4$ while maintaining the temperature at 15°–20° by means of an ice bath. The reaction was allowed to warm to room temperature and was then added to an ice/$H_2O$ mixture. The resulting soid was filtered, dissolved in toluene on a steam bath, cooled to room temperature and diluted with hexane with a solid forming. This solid was filtered and air dried to yield 3.8 g (38%). An analytical sample was prepared by treating a sample a second time as above and drying in the vacuum pistol at room temperature, m.p. 100°–101°.

Anal. Calcd. for $C_{14}H_{11}ClO_3$: C, 64.01; H, 4.22; Found: C, 63.92; H, 4.33.

What is claimed is:
1. The compound 5-[5-(4-chlorophenyl)-2-furanyl]-dihydro-2(3H)-furanone.

* * * * *